US00PP10001P

United States Patent [19]

Kientzler

[11] Patent Number: Plant 10,001

[45] Date of Patent: Aug. 12, 1997

[54] IMPATIENS PLANT NAMED 'GUADELOUPE'

[75] Inventor: Ludwig Kientzler, Gensingen, Germany

[73] Assignee: Paul Ecke Ranch, Inc., Encinitas, Calif.

[21] Appl. No.: 620,957

[22] Filed: Mar. 25, 1996

[51] Int. Cl.[6] ..... A01H 5/00

[52] U.S. Cl. ..... Plt./87.6

[58] Field of Search ..... Plt./87.6

*Primary Examiner*—Howard J. Locker

*Attorney, Agent, or Firm*—Foley & Lardner

[57] ABSTRACT

A new and distinct cultivar of Impatiens plant named Guadeloupe, chracterized by its compact growth habit with excellent branching; large (7 cm) bicolored bright fuchsia and lavender flowers; very floriferous; dark, bronze-green foliage, and adaptability to 4 " pot, 6 " pot and hanging basket culture.

1 Drawing Sheet

The present invention relates to a new and distinct cultivar of plant known as Impatiens and commercially known as New Guinea Impatiens. The new cultivar is known by the cultivar name Guadeloupe and was developed by the inventor Ludwig Kientzler in Gensingen, Federal Republic of Germany by crossing the cultivar designated K Z 334 (seed parent) with the cultivar R P 87 (pollen parent).

Asexual reproduction by terminal (stem tip) cuttings taken by or under the supervision of the inventor at Gensingen, Federal Republic of Germany, has shown that the unique features of this new impatiens are stabilized and are reproduced true to type in successive propagations.

The following characteristics distinguish the new Impatiens from both its parent varieties and other cultivars of this general type known and used in the floriculture industry:

1. Compact growth habit with excellent branching charcteristics. Plants in 16.5 cm pots were 21 cm tall and 36 cm wide, eight weeks after first flowering.

2. Large, bicolored bright fuchsia and lavender flowers. Open flowers measure up to 7 cm in diameter.

3. Very floriferous. Plants in 16.5 cm pots were in flower eight (8) weeks after planting.

4. Dark, bronze-green foliage.

5. Well suited to 4" pot, 6" pot and hanging basket culture.

Guadeloupe is similar in many respects to Octavia, disclosed in U.S. Pat. P.P. No.8,430. Although each cultivar has bicolored flowers and dark, bronze-green foliage, the flower color of Guadeloupe is a bright fuchsia and lavender, while Octavia is red and violet. Guadeloupe has a larger portion of the darker color on each flower petal. In addition, Guadeloupe has a more compact, but spreading growth habit, large flowers and a more distinct bicolor flower pattern than Octavia. These differences are based on comparisons made in May 1995 based on plants of the same age and in full flower.

The accompanying colored photographic drawing, is a top perspective view of the new cultivar, showing color as true as it is reasonably possible to obtain in a colored reproduction of this type.

The following is a detailed description of the new impatiens cultivar based on plants grown under commercial practice in Encinitas, Calif. Plants were started as rooted cuttings and were transplanted in mid-February into 16.5 cm (6.5 inch) pots, one pot per plant. By mid-April, plants were growing vigorously and were in flower. The values, measurements and observations noted below were taken from plants in full bloom in mid-May.

Color references are made to The Royal Horticultural Society Colour Chart (R.H.S.), except where general terms of ordinary dictionary significance are used.

Parentage: Cross between K Z 334 (seed) and R P87 (pollen).

Asexual reproduction:

*Cutting type.*—Tip, with stems 2–3 cm long and developing to 4–5 cm after 21 days in propagations.

*Time to initiate roots.*—8–10 days at 23° C.; nicely developed root mass in 18–21 days.

*Rooting habit.*—Numerous, fibrous, adventitious roots from the stem.

Plant description:

*Form.*—Symmetrical, bush shaped, flowering herb, with self-branching characteristics giving the plant a full appearance. Pinching is not recommended since it does not enhance branching and only delays flowering by removing flower buds.

*Habit of growth.*—Vigorous, self-branching habit, producing whorls of leaves and flowers. Growth is indeterminate and flowering is continuous.

*Foliage description.*—Leaves are simple. Lower leaves on stems in whorls of 2–3. Higher on stem, leaves in whorls of mostly 5. Leaf shape: Broadly elliptic to ovate. Leaf blade tips are acuminate; bases of immature leaves are acute; mature leaves attenuate. Leaf blade size: Mature leaves 8–10 cm long and 3–4 cm wide. Petiole length: About 1 cm. Leaf margin: Ciliated and finely serrated. Leaf texture: Slightly rugose. Upper surface: Glabrous. Under surface: Glabrous. Leaf color: Dark, bronze-green with a red midvein. Upper surface: Darker than 147A. Midvein near 53A. Under surface: Greyed purple, 183A-B. Venation: Pinnate.

Flowering description:

*Flowering habits.*—Very floriferous. Flowering is continuous. Flowers develop progressively around the whorl of leaves, taking 5–7 days from buds which show color, to bloom. Flowers are single and large, lasting for 2–3 weeks.

*Natural flowering season.*—Flowering is indeterminate and occurs throughout the year. Quantity of flowers increases with increasing light intensity and duration. However, floriferousness may wane during hot summer days in temperate climates.

*Flower buds.*—Ellipsoidal and covered with three (3) sepals plus rudimentary sepals fused into the under surface of the superior petal. A spur originates from the base of the inferior sepal. Spur is reddish and about 5 cm long.

*Flowers borne.*—Singly, on reddish green pedicels about 6 cm long.

*Quantity of flowers.*—One flower per leaf. Flowers occur progressively around the whorl of leaves so that tight buds to mature flowers are visible at the same time.

*Petals.*—The superior and lateral petals open less than perpendicularr to the pedicel and the inferior petals are reflexed so that the plane of the flower surface is not flat. Number of petals: Five (5) petals, all overlapping. Shape: All petals are heart-shaped. Superior petal has a broad base. Other petals have a pointed base. Color: Bright fuchsia and lavender bicolored petals. Upper surface: Periphery near 82D. Strip along midvein and a large portion of the superior petal near 74B. Under surface: Periphery near 72C, 5B along midvein. Flower size: Large, up to 7.0 cm in diameter.

*Reproductive organs.*—Stamens: Five (5), broad and fused to form a tube around the ovary; red in color. Anther: Hooded and cream colored. Pollen: Cream colored. Stigma: Five-pointed star, colorless. Styles: Very short. Ovary: Five-celled, 4–5 mm long until fertilized. Grows to 1 cm or longer after fertilization; purplish.

Resistance to disease: Good resistance to common stem and root diseases, Rhizoctonia and Pythium. Botrytis may be a problem in humid or mist propagation environments, but no greater than with other New Guinea Impatiens cultivars.

It is claimed:

1. A new distinct cultivar of Impatiens plant named Guadeloupe, as illustrated and described.

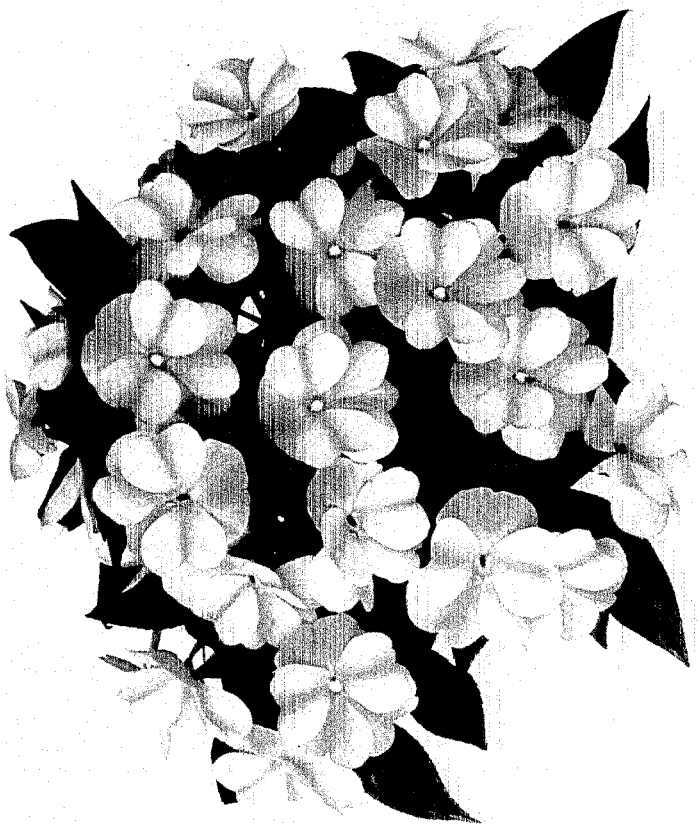

* * * * *